United States Patent [19]

Rau et al.

[11] Patent Number: 4,465,828

[45] Date of Patent: Aug. 14, 1984

[54] PROCESS OF PREPARING ALKYLSACCHARIDES

[75] Inventors: Allen H. Rau; Donald T. Speckman, both of Cincinnati, Ohio

[73] Assignee: The Procter & Gamble Company, Cincinnati, Ohio

[21] Appl. No.: 580,282

[22] Filed: Feb. 17, 1984

Related U.S. Application Data

[63] Continuation of Ser. No. 452,647, Dec. 23, 1982, abandoned.

[51] Int. Cl.$^3$ .......................... C07G 3/00; C07H 1/00; C08B 37/00
[52] U.S. Cl. .................................. 536/18.6; 536/124; 536/127
[58] Field of Search ....................... 536/18.6, 124, 127

[56] References Cited

U.S. PATENT DOCUMENTS 3,766,165  10/1973  Rennhard .......................... 536/18.6

Primary Examiner—Donald B. Moyer
Assistant Examiner—C. Joseph Faraci
Attorney, Agent, or Firm—Robert B. Aylor; Thomas H. O'Flaherty; Richard C. Witte

[57] ABSTRACT

Hydroxy carboxylic acids minimize the formation of color bodies in processes for preparing and purifying alkylsaccharides when the temperature exceeds about 100° C.

19 Claims, No Drawings

PROCESS OF PREPARING ALKYLSACCHARIDES

This is a continuation of application Ser. No. 452,647 filed on Dec. 23, 1982 now abandoned.

TECHNICAL FIELD AND BACKGROUND ART

This invention relates to an improved process for making alkylsaccharides in which the alkyl group contains from about 1 to about 20 carbon atoms and the saccharide portion contains from about 1½ to about 30 saccharide units. The improved process provides an alkylsaccharide product with improved color.

U.S. Pat. No. 4,341,809, discloses a stabilized starch composition prepared by adding a buffer to a slurry of starch and then drying the starch-buffer slurry. All of the materials taught are alkaline to protect against acid degradation.

SUMMARY OF THE INVENTION

The present invention relates to a process for preparing an alkylsaccharide. It has been discovered that hydroxypolycarboxylic acids added at low levels, either during the formation of the alkylsaccharide or later during the subsequent cleanup processes, minimizes the formation of colored materials. Thus, the invention relates to the process for producing an alkylsaccharide by reacting an alcohol and a reducing sugar containing from 5 to 6 carbon atoms, or source thereof, in the presence of a strong acid catalyst comprising adding to the reaction mixture from about 0.0015% to about 1%, preferably from about 0.0075% to about 0.1%, more preferably from about 0.02% to about 0.05% of a hydroxy polycarboxylic acid, preferably in the form of a hydrate and/or the process for heating an alkylsaccharide in the presence of from about 0.003% to about 2%, preferably from about 0.02% to about 0.2%, more preferably from about 0.04% to about 0.1% of a hydroxy polycarboxylic acid, or salt thereof, selected from the group consisting of citric acid, tartaric acid, maleic acid and mixtures thereof.

Processes for making the alkylsaccharides of this invention are described in U.S. Pat. Nos. 3,219,656 Boettner et al; 3,219,656 Boettner; 3,598,865, Lew; 3,707,535, Lew; 3,772,269, Lew; and 3,839,318, Mansfield, all of said patents being incorporated herein by reference. A preferred process is disclosed in U.S. patent Application Ser. No. 371,698, filed Apr. 26, 1982 of Mark H. K. Mao entitled PROCESS OF PREPARING ALKYLPOLYSACCHARIDES, said application being incorporated herein by reference.

When the hydroxypolycarboxylic acids, or salts thereof, are incorporated into the reaction mix, preferably in the form of their hydrates, the color of the resulting alkylsaccharide is improved. Although it is not desired to be bound by theory, it is believed that these hydroxypolycarboxylic acids act as buffers and water sinks and, when used as hydrates, sources of controlled water addition.

After the preparation of the alkylsaccharide and neutralization of the acid catalyst used in the formation of the alkylsaccharide, the hydroxypolycarboxylic acids or their salts act as buffering agents in any subsequent processing steps. By maintaining the pH of the alkysaccharide within a range of from about 3 to about 10, preferably from about 5 to about 7, excess degradation of the alkylsaccharide and formation of color bodies is minimized even when the alkylsaccharide is exposed to high temperatures, e.g., from about 110° to about 165° C.

DETAILED DESCRIPTION OF THE INVENTION

The alcohols useful in the formation of the alkylsaccharides of this invention include fatty alcohols containing from one to about 20 carbon atoms which can be primary or secondary alcohols having straight or branched chains which can be either saturated or unsaturated and may contain ether linkages. Preferably the alcohols are primary saturated alcohols including as specific examples, dodecyl, tridecyl, tetradecyl, pentadecyl, hexadecyl, octyadecyl alcohols and mixtures thereof. The preferred fatty alcohols are those containing from about 10 to about 16 carbon atoms. However, in addition to these longer chain fatty alcohols, shorter chain alcohols, such as methanol, ethanol, propanol, butanol, ethylene glycol, propylene glycol, and glycerine can be used and, in fact, are desirable for many uses. The alcohol can also contain benzene rings so that the alcohol can be a phenol.

The saccharide portion of the molecule can be derived from fructose, glucose, mannose, cylose, osose, lyxose, ribose and mixtures thereof. The preferred saccharides are glucose and fructose due to their availability and low cost and the most preferred saccharide is derived from glucose. Preferably the reaction to form the alkylsaccharide is carried out at a temperature of from about 90° to about 130° C. Preferably the temperature is kept below about 120° C. to minimize formation of color materials.

Auxiliary solvents can be used, including toluene, $C_{8-12}$ hydrocarbons, etc.

Preferably the reaction takes place in a thin-film, preferably at high Reynolds numbers to permit a rapid reaction and improved heat transfer, thereby minimizing the time to which the saccharide is exposed to high temperatures. Thin-films can be achieved in wiped-film evaporators, drum evaporators or mills in which two cylinders combine to form a thin film.

Acid catalysts useful in the preparation of alkylsaccharides include such conventional acids as sulfuric, hydrochloric, phosphoric, phosphorus, toluene sulfonic, etc. Other Lewis acid catalysts can be used. The amount of acid catalyst used is normally between about 0.001 and about 0.1 moles per mole of saccharide monomer, preferably between about 0.005 and about 0.05, most preferably between about 0.005 and about 0.025. The amount of catalyst used can control the speed of reaction. Sulfuric acid is the preferred catalyst.

All ratios, percentages, and parts herein, are by weight unless otherwise specified.

EXAMPLE 1

Alkylpolysaccharides were prepared by combining 100 g. of anhydrous dextrose; 165 g. of fatty alcohols containing primarily 12 or 13 carbon atoms; 403 g. of butanol; 0.52 g. p-toluene sulfonic acid; and the indicated acids which were added after the dextrose. The reaction mixes were quickly heated to butanol's boiling point about 115°–118° C. (239°–244° F.) and allowed to reflux for one hour. Then, the butanol was removed by partial vacuum at a minimum temperature of about 93° C. (200° F.). Vacuum was increased to 2 mm Hg. and the temperature allowed to rise to about 115° C. (239° F.) for 30 minutes. The reaction mix was then cooled and neutralized with 0.27 g. sodium carbonate dissolved in 2.5 g. H₂O. The percent transmission (Coleman Color at 470 nm in a 25×105 nm cell of a 50% solution in butanol) was measured.

|     |                              | % Transmission |
| --- | ---------------------------- | -------------- |
| A.  | Control (no acid added)      | 27             |
| B.  | 5.5 g. citric acid hexahydrate | 48           |
| C.* | 3.91 g. tartaric acid        | 43             |
| D.* | 2.76 g. maleic acid          | 47             |

*centrifuged to remove haze.

As can be seen from the above, the presence of the acids improves the color. When the alkylpolysaccharide product is exposed to a temperature of above 120° C. in subsequent processing steps, including distillation of the unreacted fatty alcohol, similar results are obtained in that the products admixed with the citric, tartaric, and/or maleic acids discolor much more slowly.

What is claimed is:

1. In the process for producing an alkylsaccharide by reacting an alcohol with a reducing sugar containing from 5 to 6 carbon atoms, or source thereof, in the presence of a strong acid catalyst, the improvement of incorporating in the reaction mixture from about 0.0015 to about 1% of hydroxy polycarboxylic acid, selected from the group consisting of citric acid, maleic acid, tartaric acid, salts of said acids, hydrates of said acids, and mixtures thereof.

2. The process of claim 1 wherein said hydroxypolycarboxylic acid is present in the form of a hydrate initially.

3. The process of claim 1 wherein said hydroxypolycarboxylic acid is citric acid.

4. The process of claim 3 wherein said citric acid is present initially as a hydrate.

5. The process of claim 1 wherein said hydroxypolycarboxylic acid is maleic acid.

6. The process of claim 5 wherein said maleic acid is present initially as a hydrate.

7. The process of claim 1 wherein said hydroxypolycarboxylic acid is tartaric acid.

8. The process of claim 7 wherein said tartaric acid is present initially as a hydrate.

9. The process of claim 1 wherein said hydroxypolycarboxylic acid is present at a level of from about 0.0075% to about 0.1%.

10. The process of claim 9 wherein said hydroxypolycarboxylic acid is present at a level of from about 0.02% to about 0.05%.

11. The process of claim 9 wherein said hydroxypolycarboxylic acid is citric acid.

12. The process of claim 11 wherein said citric acid is present initially as a hydrate.

13. In the process of heating an alkylsaccharide to a temperature above 120° C. to about 165° C. wherein the saccharide portion of said alkylsaccharide is derived from a reducing sugar containing five or six carbon atoms, the improvement of incorporating from about 0.003 to about 2% of a hydroxy polycarboxylic acid selected from the group consisting of citric acid, tartaric acid, maleic acid, and mixtures thereof.

14. The process of claim 13 wherein the mixture of the alkylsaccharide and hydroxypolycarboxylic acid has a pH from about 3 to about 10.

15. The process of claim 14 wherein said pH is from about 5 to about 7.

16. The process of claim 15 wherein the pH of the mixture of said alkylsaccharide and said hydroxypolycarboxylic is from about 5 to about 7.

17. The process of claim 13 wherein said hydroxypolycarboxylic acid is citric acid.

18. The process of claim 13 wherein said hydroxypolycarboxylic acid is tartaric acid.

19. The process of claim 13 wherein said hydroxypolycarboxylic acid is maleic acid.

* * * * *